United States Patent [19]
Genest

[11] Patent Number: 4,531,526
[45] Date of Patent: Jul. 30, 1985

[54] REMOTE SENSOR TELEMETERING SYSTEM

[76] Inventor: Leonard J. Genest, 1061 Tropic La., Santa Ana, Calif. 92705

[21] Appl. No.: 527,376

[22] Filed: Aug. 29, 1983

Related U.S. Application Data

[63] Continuation of Ser. No. 290,746, Aug. 7, 1981, abandoned.

[51] Int. Cl.³ .............................................. A61B 5/00
[52] U.S. Cl. ..................................... 128/630; 128/903
[58] Field of Search .................. 128/419 PS, 419 PT, 128/631, 630, 695, 696, 702, 703, 704, 705, 706, 707, 708, 736, 903

[56] References Cited

U.S. PATENT DOCUMENTS

| | | | |
|---|---|---|---|
| 3,229,684 | 1/1966 | Nagumo et al. | 128/631 |
| 3,572,324 | 3/1971 | Petersen | 128/706 |
| 3,872,455 | 3/1975 | Fuller et al. | 128/903 |
| 4,223,679 | 9/1980 | Schulman et al. | 128/419 PT |

Primary Examiner—William E. Kamm
Attorney, Agent, or Firm—Nilsson, Robbins, Dalgarn, Berliner, Carson & Wurst

[57] ABSTRACT

A telemetering system for remotely measuring a physical parameter of an object such as a human or animal includes a sensor device affixed to the object including a tuned circuit and a parameter sensitive device coupled for altering the figure of merit of energy storage (Q) of the tuned circuit in response to variations in the physical parameter, and an indicator unit for transmitting a signal to intermittently ring or energize the tuned circuit with a burst of oscillating electromagnetic energy and sense the resultant reradiated ring signal generated by the tuned circuit. The indicator unit measures the rate of decay of the sensed reradiated ring signal after the end of each transmitted energy burst as a measure of the Q of the tuned circuit. The indicator unit includes a microprocessor which generates a measure of the rate of decay and then computes the measure of the physical parameter according to a prestored functional relationship between the physical parameter measure and the decay rate of sensed ring signal. The computed measure is then displayed in a display device. A phase locked loop circuit in the indicator unit is coupled to alter the phase and hence the frequency of the transmitted signal to be in phase with the resonant frequency of the tuned circuit. The decay rate may be measured by generating a ratio of peak voltage values sampled at two different but predefined times after the sensed ring signal begins decaying.

42 Claims, 10 Drawing Figures

REMOTE SENSOR TELEMETERING SYSTEM

This is a continuation of application Ser. No. 290,746, filed Aug. 7, 1981, now abandoned.

BACKGROUND OF THE INVENTION

The present invention relates to telemetering systems and in particular to a telemetering system which measures a physical parameter of a body by sensing variations in the figure-of-merit of energy storage (Q) of the sensor circuit caused by variations in selected parameter.

Telemetering systems for detecting the temperature, blood pressure, or other physical parameter of a human or animal patient from a remote location are known. For example, a miniature adjustable telemetering device is disclosed in Pope, et al., U.S. Pat. No. 3,971,362 as including a thermistor in a sensor circuit to measure body temperature. The sensor circuit generates intermittent bursts of energy at its resonant frequency where the time interval between bursts in dependent upon the resistance of the thermistor so that measurement of the interval between pulses constitues a measurement of the temperature of the object. An external device is utilized to detect the burst of energy from the sensor circuit and measure the time interval between the bursts. Therefore, Pope, et al does not measure variations in the Q of the sensor circuit to obtain a temperature value of the object.

Other references disclosing somewhat similar devices to the Pope, et al. device include Fryer, U.S. Pat. No. 3,453,546, and Murate, U.S. Pat. No. 3,682,160. For example, in Fryer, the ratio between a constant time interval and a time interval which varies dependent on the temperature is measured as a means of measuring temperature. Murata uses a similar system to measure acidity. Neither of these systems rely on sensing variations in the Q of the sensor circuit to measure the physical parameter, however.

A system utilizing a passive sensor device which is rung at the resonant frequency by an oscillating transmitted signal is disclosed in Honig, U.S. Pat. No. 3,218,638. However, in that system, the sensor circuit requires a pair of resonant tank circuits, one having a fixed resonant frequency and the other having a resonant frequency which varies in response to the resistance of a thermistor. A temperature measurement is obtained by comparing the fixed resonant frequency against the variable resonant frequency. Honig therefore does not measure variations in the Q of the sensor circuit.

Another patent which discloses the concept of sensing the ringing of a tuned sensor circuit is Nagumo, et al., U.S. Pat. No. 3,229,684. The sensor circuit in Nagumo stores energy from the transmitted signal and then reradiates that energy only after a period of time has elapsed after the termination of the transmitted energizing signal burst. The time period between the termination of the transmitted signal and initial reradiation of the signal is dependent on the value of a circuit component which is parameter sensitive so that the delay time constitutes a measurement of the parameter. Therefore, Nagumo likewise does not measure sensor circuit Q to indicate the value of the parameter.

The above-identified devices basically fall into one the two categories. In the first category, the devices rely on measuring frequency shifts. However, all such devices require extremely accurate and precise components which are either unavailable or are too expensive to be practical. Furthermore, such devices lack stability in operation.

In the second category are devics which measure variable pulse widths. However, these devices also suffer serious stability drawbacks and in any event use active components which inherently result in complex circuits and usually require a power supply.

By contrast, the present system and method utilizes an entirely passive sensor circuit which is first attached to an object and which is intermittently energized or rung at its resonant frequency by an oscillating signal burst from a remote indicator unit. The sensor circuit temporarily stores the energizing energy and then reradiates that energy. The rate of decay of the reradiated ring signal after each signal burst varies depending on the Q of the sensor circuit which is dependent, for example, upon the resistance of the thermistor and hence the temperature of the body with which the thermistor is in contact. The rate of decay of the ring signal is sensed and processed by the remote indicator unit to obtain a value of Q and therefrom the parameter value, such as temperature, which is then displayed.

Thus, the present invention does not suffer from the instabilities and complexity of prior art devices.

SUMMARY OF THE INVENTION

A telemetering system for measuring a selected physical parameter of an object and method in accordance with the invention includes an indicator device and a passive tuned sensor circuit. The passive sensor circuit is attached to the object and has a Q which varies in response to variations in the physical parameter. The indicator device includes an oscillating signal generator which generates a first signal which functions as a clock signal for a microprocessor. The first signal is also intermittently sampled and transmitted to provide intermittent signal bursts each of which comprises a selected number of oscillations of the first signal. The indicator device also includes a receiver which receives a second oscillating signal generated by the sensor circuit in response to the transmitted burst. The indicator unit includes means for measuring variations in the Q (figure of merit of energy storage) of the sensor circuit due to variations in the physical parameter. The means for measuring variations in Q relies in one embodiment on the fact that the rate of decay of the second signal after cessation of the first signal burst is related to the Q of the circuit so that measurement of the rate of decay is a measurement of the Q of the circuit. By comparing and relating a measured rate of decay to a standard or fixed value, a difference, which is a predefined function of the physical parameter, can be used as an input to a function generator or suitable look up table in a microprocessor to obtain the value of the parameter. Such a process comprises one illustration of the method in accordance with the invention.

In one specific means of measuring the rate of decay, one of the oscillations of the second signal occurring after the end of each signal burst is selected utilizing suitable selecting means. The peak value of the selected oscillation is measured in a peak value sample-and-hold circuit with the sampled value being digitized and processed in a microprocessor according to a predefined functional criteria to compare and relate to a fixed value as stated above and to generate a value of the selected physical parameter of the object. Means are provided for displaying the generated parameter value.

The telemetering system sensor circuit includes a tuned circuit which is rung by each signal burst from the indicator device and a parameter sensitive component coupled in the tuned circuit. The tuned circuit continues ringing after the end of the signal burst thereby causing the decaying second signal to be transmitted from the sensor circuit. The parameter sensitive component may be a thermistor to measure temperature or may be any other parameter sensitive device coupled in the tuned sensor circuit for altering the Q of the circuit and therefore the rate of decay of the second signal. In the above described specific means of measuring, the amplitude of the received second signal is first normalized so that its amplitude at a specific time will be constant regardless of variations in sensor circuit Q. At a fixed time interval thereafter, the peak amplitude of a selected oscillation of the second signal is measured. The peak amplitude of that oscillation of the second signal is then a measure of the decay rate and hence the Q of the circuit.

The tuned circuit includes a capacitor and an inductor coupled in parallel with the capacitor. If the parameter sensitive member is a thermistor, it is coupled in parallel across both the capacitor and inductor. Alternatively, the parameter sensitive member may be a capacitor or an inductor where the dielectric of the capacitor or the core of the inductor is parameter sensitive.

In the above specific embodiment, the telemetering system indicator device may further include a phase-locked-loop means which is coupled to adjust the phase (and therefore the frequency) of the first oscillating signal until it is in phase with the second received signal. When the two signals are in phase (and at the same frequency, a) "phase compare" signal is generated. The microprocessor senses the "phase compare" signal to enable the display of the parameter measurement. Thus, errors due to phase and frequency mismatch will be eliminated before the value of the parameter will be displayed.

The indicator device of the telemetering system may also include a variable amplifier means coupled to the receiver amplifier for varying the amplitude of the second signal so that the amplitude of the second signal at a predetermined initial time will match a predefined value. A means for selecting another of the oscillations of the second signal outputted from the receiver amplifier is provided for sampling and measuring the peak value of the selected other oscillation. The resultant peak value of the second signal at the predetermined time is compared in a means for comparing against a predefined calibration value stored in the microprocessor. A gain control signal is generated if the difference between the resultant peak value and the calibration value is greater than a predefined tolerance value. The resultant gain control signal is converted to an analog signal which is coupled to alter gain of the receiver amplifier. A suitable compare signal is generated to enable a display device if the resultant peak value of the selected oscillation matches the calibration value. Display of the parameter value is enabled by the compare signal.

BRIEF DESCRIPTION OF THE DRAWINGS

A complete understanding of the invention and the above advantages thereof can be gained from a consideration of the following description of the preferred embodiments taken in conjunction with the drawings in which.

DETAILED DESCRIPTION

Figure 7:
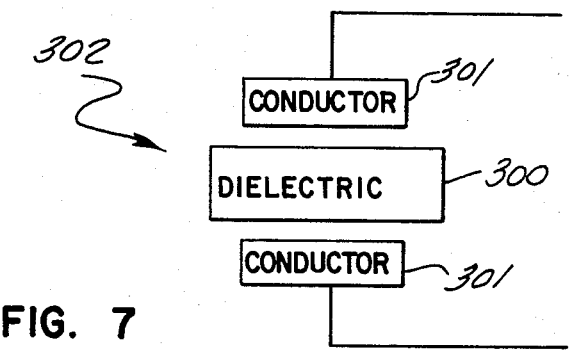
FIG. 7 is a capacitor with a parameter sensitive dielectric.
Figure 8:
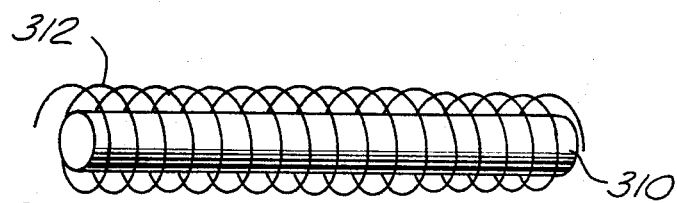
FIG. 8 is an indicator with a parameter sensitive inductor.
Figure 9:
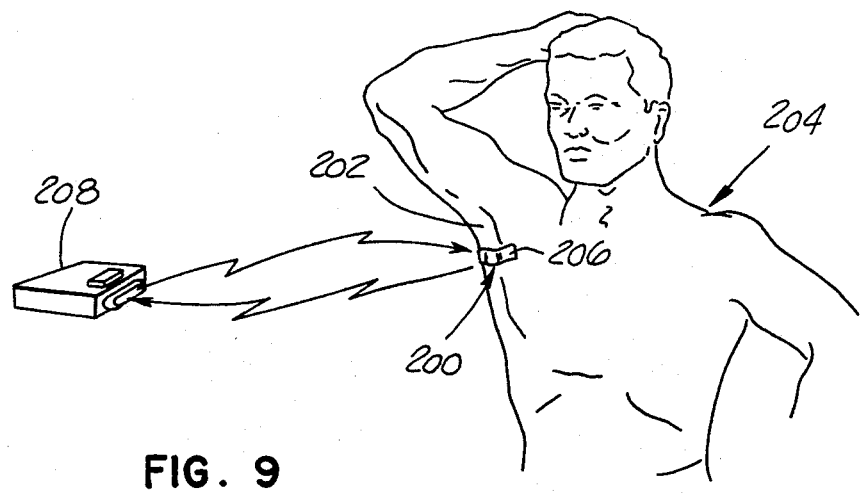
FIG. 9 is an illustration of the method of remotely measuring the selected parameter in accordance with the invention.

The present invention is a system particularly useful in taking the temperature of a human or animal patient without invading or otherwise disturbing the patient but which may be used to remotely measure any other physical parameter of either an animate or inanimate object. Referring to FIG. 9, the method according to the invention includes attaching a small, low-cost, disposable, remote and passive sensor device 200 such as illustrated in FIGS. 2-7 and 8, to the axilla area 202 of the patient's body 204 by means of an adhesive strip or bandage 206. The sensor device 200 is then energized by and a portable, hand-held indicator unit 208 to cause the sensor device to store energy and then reradiate that energy as the "ring" signal. Thereafter the ring signal is remotely sensed by the indicator unit 208 which receives the reradiated signal from the sensor. The indicator unit then processes the received ring signal to obtain a measure of the Q of the sensor and therefrom to generate a temperature value. The indicator unit will preferably interact with a sensor device when brought within a proximity of about 9 to 12 inches without the necessity of touching or upsetting the patient. Therefore, the method and system is noninvasive, does not cause contamination and provides a virtually instantaneous reading because the sensor device will already be at the temperature of the body for which a reading is desired. Further, the sensor device may be discarded after use by one patient because of its low cost.

Functionally, the indicator unit consists of a transmitter, a receiver and suitable processing circuitry.

The indicator unit transmitter is interconnected to the processing circuitry to produce intermittent bursts of energy which energize the sensor device through the mutual inductance of the transmitter coil and an inductor coil in the sensor device. The sensor device is simply a parallel tuned circuit and a parameter sensitive device connected so that variations in the parameter cause the Q of the sensor circuit to vary. In one embodiment, the tuned circuit may be shunted by a thermistor where the figure-of-merit of energy storage, Q, of the sensor device is a function of the resistance value of the thermistor. Since the resistance of the thermistor is a function of its temperature, and since variations in the thermistor resistance alter the Q of the sensor device, measurement of the Q will indicate the temperature of the patient.

To measure the Q of the sensor circuit, a burst of oscillating energy from the indicator unit transmitter is coupled to the sensor circuit through the mutual inductance of the transmitter and sensor coils to cause the sensor circuit to ring at its resonant frequency. At the termination of each transmitted burst of oscillating energy, the signal retransmitted from the tuned sensor circuit decays at a rate which is a function of the Q of the sensor circuit. Therefore, it is merely necessary to measure the decay rate of the ring signal received from sensor circuit and use that value in a function generator or look-up-table which defines the fixed relationship between temperature (or any other parameter) and the decay rate, to generate a value of temperature. One method of measuring decay rate is to measure the magnitude of the decaying signal received by the indicator unit at two different times after the termination of the trasmitted burst and compute a decay rate based upon the magnitude of the difference and the time period between samples. For example, the indicator unit may be configured to first normalize the peak amplitude value of a specified oscillation of the ring signal and then to subsequently measure and process the peak value of the received ring signal to generate and display a digital temperature reading.

Figure 1:
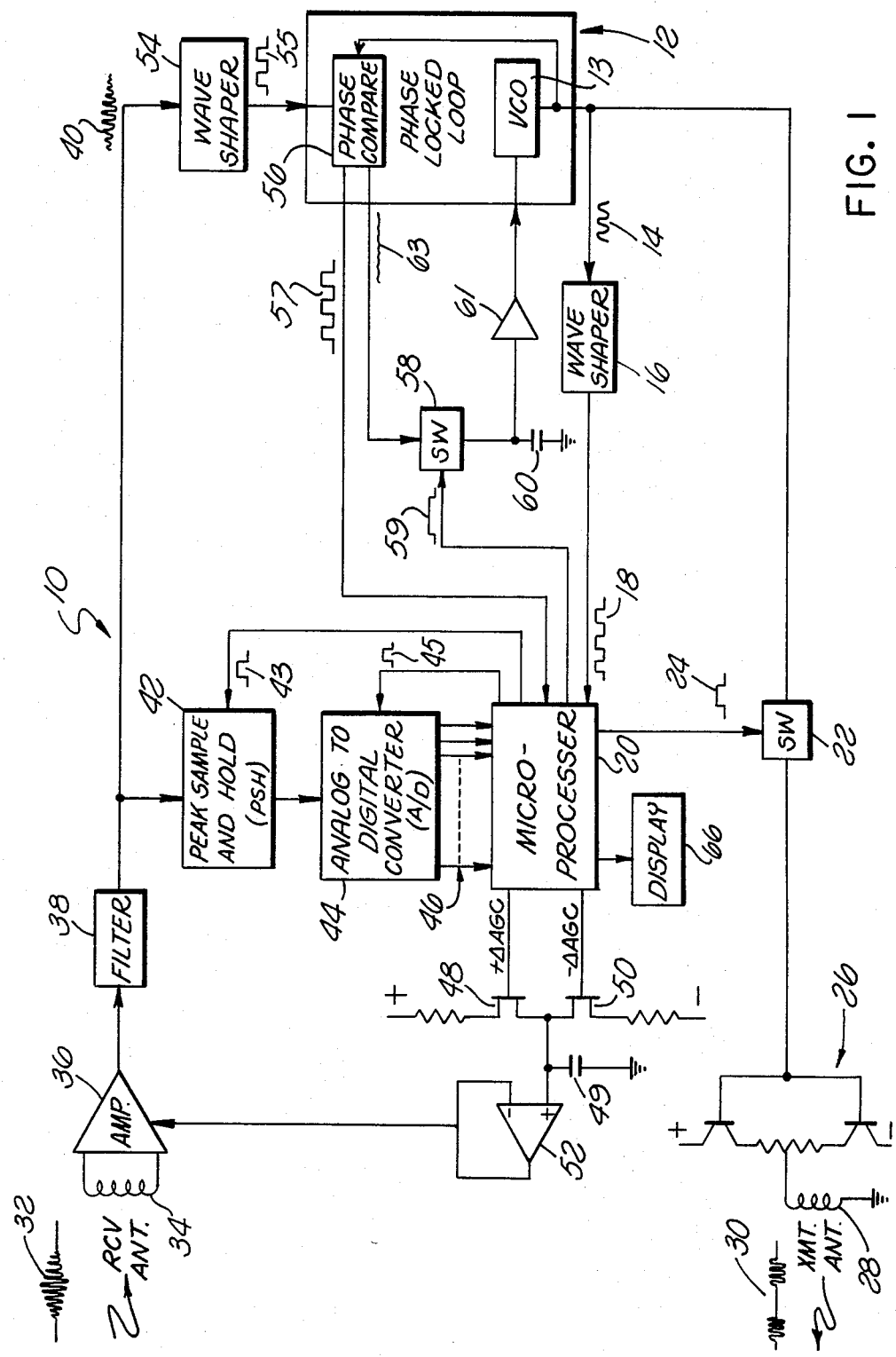
FIG. 1 is a block diagram of one embodiment of an indicator unit in accordance with the invention.
Figure 5:
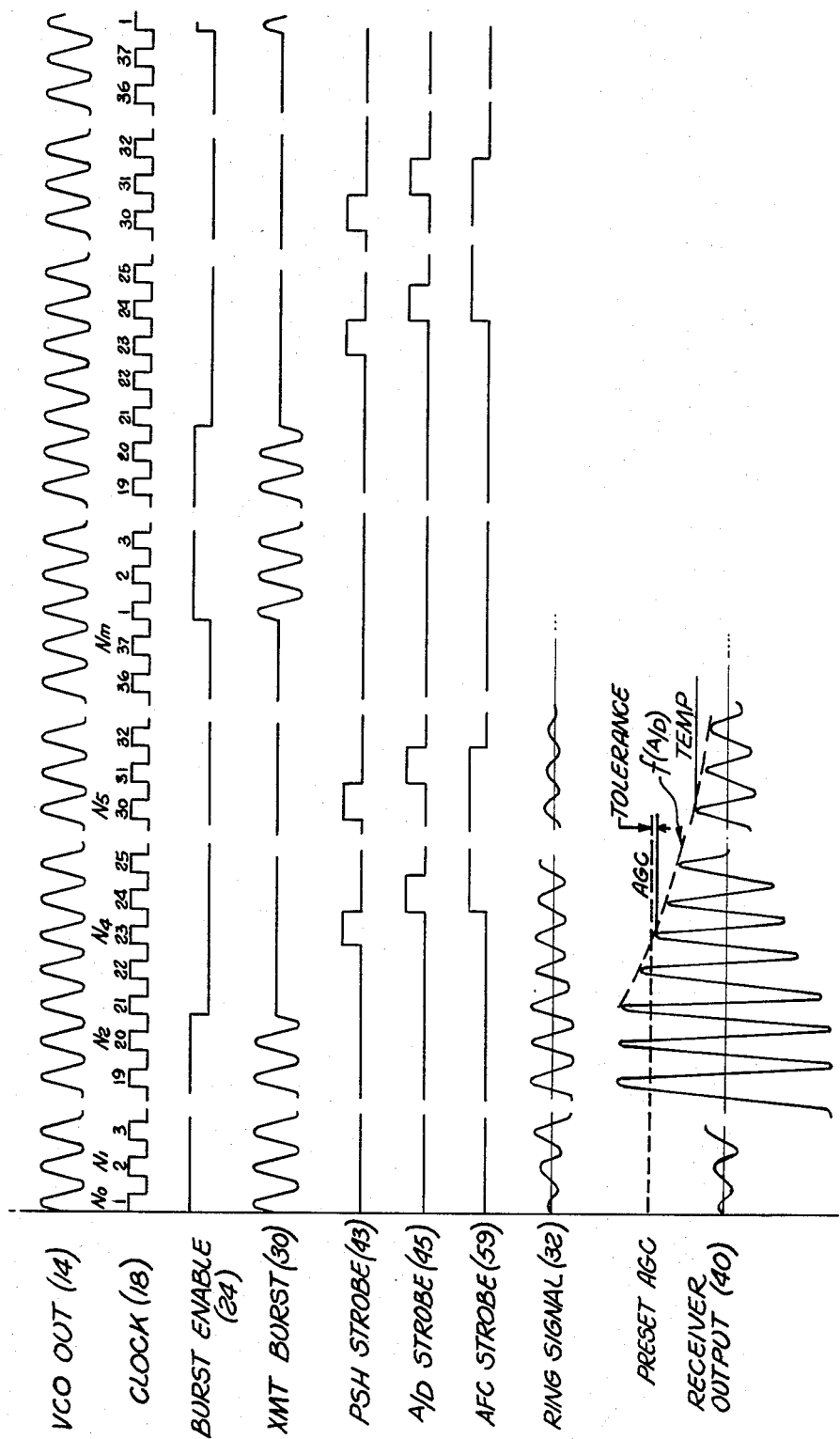
FIG. 5 is a signal time diagram illustrating the wave shapes of a number of signals in the indicator unit of FIG. 1.

Referring now to FIG. 1, one illustrative embodiment of an indicator unit 10 operating in accordance with the invention includes a phase-locked-loop 12 having a voltage controlled oscillator (VCO) 13 which generates a first or VCO output signal 14. The VCO output signal 14 may have a wave shape as shown in FIG. 5 or any other convenient periodic wave shape. The VCO output signal 14 may be coupled to a suitable wave shaper 16 to generate a clock signal 18 having a square wave shape as shown in FIG. 5. The clock signal 18 is coupled to a microprocessor 20 which includes a suitable counter for counting the clock signal pulses and generating various strobe and enable signals in a manner to be described hereafter.

The VCO output signal 14 is also coupled to an analog switch 22 which is intermittently opened and closed in response to a burst enable signal 24 generated by the microprocessor 20. The burst enable signal 24 comprises a pulse which remains at, for example, a high-voltage level so long as the count on the microprocessor 20 is less than a predefined number such as twenty as illustrated by the wave shape shown in FIG. 5. While switch 22 is closed, the VCO output signal is transmitted from a transmitter antenna coil 28 of a transmitter 26. If the count on the microprocessor counter is greater than twenty, however, the switch 22 is open and a VCO ouput signal burst will not be transmitted. The resultant burst of the VCO output signal 14 when the switch 22 is closed produces a transmitter burst signal 30 which has a wave shape illustrated in FIG. 5.

Of course, it will be appreciated that the above-described method of transmitting a burst of oscillating energy is illustrative only and various other techniques may be utilized to achieve the same result. For example, the VCO output signal 14 may be a square wave signal rather than a sine wave signal as illustrated, in which case a wave shaper such as the wave shaper 16 is unnecessary. The transmitter burst signal 30 will then have a square wave shape rather than a sine wave shape. Additionally, the transmitter burst signal may continue for a greater or lesser number of cycles than the twenty cycles used for illustrative purposes above.

Figure 2:
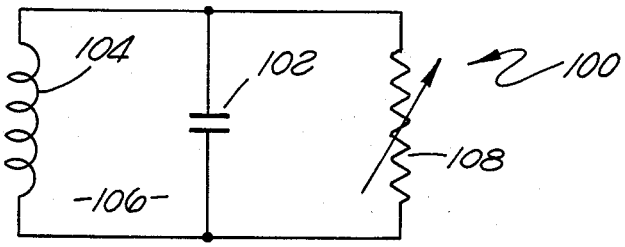
FIG. 2 is a circuit diagram of a sensor circuit in accordance with the invention.

Referring momentarily to FIG. 2, a sensor circuit 100 in accordance with the invention includes a stable capacitor 102 coupled in parallel with an inductor 104 to define a parallel tuned circuit 106. The parallel tuned circuit 106 is shunted by a suitable parameter sensitive device such as a thermistor 108. In one embodiment, the value of the capacitor 102 and indicator 104 are chosen so that the resonant frequency of the tuned circuit 106 is about 300 kilocycles (KCs). Of course, the selected resonant frequency can be altered by simply changing the component values for the capacitor 102 and inductor 104. The frequency of the VCO signal 30 and the resonant frequency of the sensor circuit 100 are selected to be as close as possible. For example, once a frequency is selected for the indicator unit, the component values of the sensor circuit are selected so that resonant frequency will be within as much as about ±30% and preferrably ±10% of the indicator unit frequency. The acceptable variation will depend on the capability of the sensor circuit to generate a ring signal in response to signals from the indicator unit having frequencies different from the resonant frequency and the capability transmitted signal to match the resonant frequency of the sensor circuit.

Figure 3:
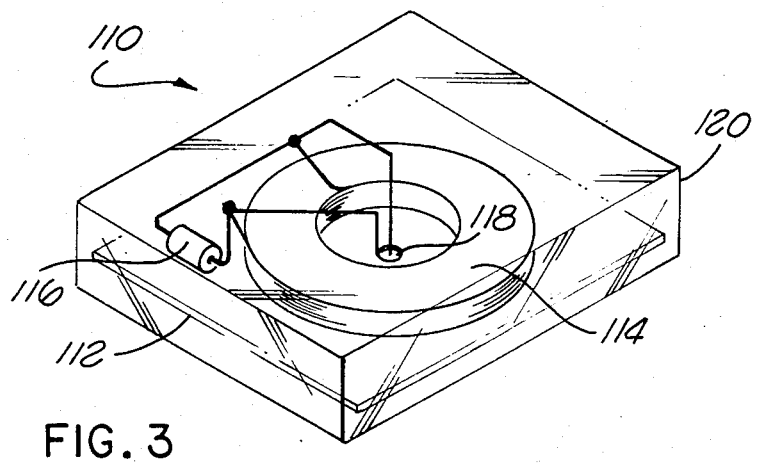
FIG. 3 is a pictorial illustration of a sensor device having the circuit configuration illustrated in FIG. 2.

Referring to FIG. 3, one physical embodiment of the sensor device in accordance with the circuit shown in FIG. 2 is the sensor 110 which comprises a printed circuit board 112 approximately one inch long by three-quarter inch wide. An inductor 114 and capacitor 116 are connected in parallel and are mounted on top of the printed circuit board 112. A suitable thermistor 118 is then mounted either on the bottom, i.e., the patient facing, side of the printed circuit board 112 or in a cavity in the bottom of the board 112, and is electrically coupled in parallel with the capacitor 116 and inductor 114. The resultant assembly is then sealed with a dipped epoxy coating 120 and is mounted onto a bandage (not shown) ready for application to the underarm area, the abdomen or other suitable location so that the thermistor 118 is adjacent, and in temperature sensing relationship, to the body whose temperature is to be sensed.

Figure 4:
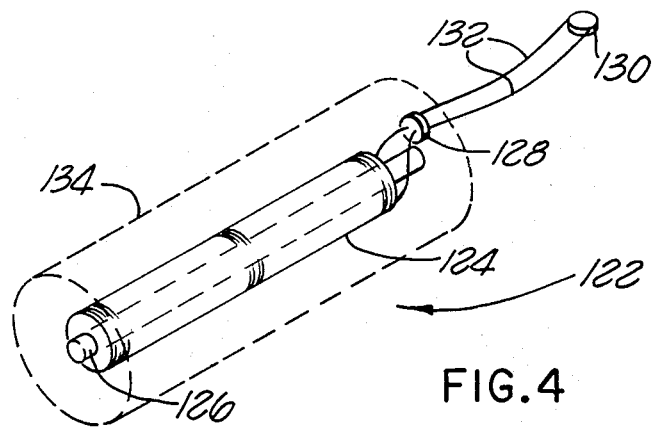
FIG. 4 is a pictorial illustration of another sensor device having the circuit configuration illustrated in FIG. 2.

Another illustrative sensor device 122 which is useful as an ear temperature sensor device is illustrated in FIG. 4, and includes a coil 124 wound on a small powdered ferrous metal rod 126 with a capacitor 128 coupled in parallel with the coil 124. The capacitor 128 may be epoxied to one end of the rod 126 for mechanical assembly. A suitable thermistor 130 is coupled in parallel across the coil 124 and the capacitor 128 utilizing two insulated wires 132 about one inch long. The resultant assembly is mounted in an open foam jacket 134 which can be inserted into the ear with the termistor positioned in contact with or very close to the tympanic membrane for very accurate temperature measurements. The use of the open cell foam jacket 134 allows the wearer to continue to hear and also permits air circulation while the sensor device 122 is in the patient's ear.

While two specific embodiments of temperature sensor devices have been illustrated in FIGS. 3 and 4, it will be appreciated that various other configurations are possible without departing from the spirit of the invention. Additionally, while the circuit shown in FIG. 2 incorporates a thermistor 108 for measuring temperature, it will be appreciated that any other parameter sensing device may be utilized. For example, a resistive, capacitive or inductive component may be coupled to the tuned circuit in such a way that the component is sensitive to variations in a selected parameter such as acidity, temperature or pressure, to cause the Q of the tuned circuit to vary. The Q of the circuit may be varied by incorporating a parameter sensitive dielectric 300 between a pair of conductors 301 in a capacitor 302 as illustrated in FIG. 7. Alternatively, as illustrated in FIG. 8, a parameter sensitive core 310 may be used in an inductive coil 312 to effect a variation in the Q of the sensor circuit in response to variations in the parameter.

Returning to FIG. 1 in conjunction with FIG. 2, the transmitter burst signal 30 from the indicator unit 10 will cause the sensor circuit 100 to ring at its resonant frequency causing the inductor 104 to transmit a ring signal 32 back to the indicator unit 10.

The ring signal 32 generated by the ringing of the sensor circuit 100 is an oscillating signal where each oscillation peak has an amplitude greater than the prior peak until the cycle-to-cycle peak amplitude is constant. In the preferred embodiment, each burst of energy transmitted from the transmitter 26 must be sufficiently long to allow the peak amplitude of the ring signal 32 to reach an equilibrium.

When the transmitted burst terminates, the sensor circuit is no longer energized and the ring signal 32 will decay at a rate which is determined by the figure-of-merit of energy storage (Q) of the sensor circuit. The figure-of-merit of energy storage is, in turn, proportional to the resistance of the thermistor which varies in response to the temperature of the body against which the thermistor is placed. Therefore, the function of the receiver portion of the indicator unit 10 is to measure the rate of decay of the received ring signal and derive a temperature value from that measurement.

The measurement of the decay rate can be accomplished in any of a number of ways in accordance with the invention in its broader aspects. For example, in the system illustrated in FIG. 1, the sensor signal 32 is received by a receiver antenna coil 34 which is placed in sufficiently close proximity to the sensor circuit 100 to receive the sensor signal 32 but at 90° relative to the transmitter coil 28 to minimize the amount of transmitted signal picked up by the receiver antenna. The received sensor signal 32 is then amplified in a variable gain amplifier 36. Undesired noise at frequencies other than a selected band of frequencies about the resonant frequency of the sensor circuit are filtered out in filter 38. The amplifier 36 is a conventional variable gain amplifier and the filter 38 is any suitable filter and may for example be a capacitor network which essentially shorts or disconnects all frequencies except the desired frequencies. The resultant receiver output signal 40 from the filter 38 has a wave form illustrated in FIG. 5.

In accordance with the embodiment of FIG. 1, the amplitude of the receiver output signal 40 is normalized by adjusting the gain of the amplifier 36 so that the peak amplitude of the received ring signal at a particular defined point in time will always be equal to a predefined voltage value. Such normalization permits the measurement of the decay slope by simply measuring the peak value of the received ring signal 40 at some later defined time after termination of the transmitted burst. Of course, it is also possible to adjust the amplitude of the transmitted signal to achieve the desired normalized amplitude value of the received ring signal.

To adjust the receiver amplifier gain, the output of filter 38 is coupled to a peak sample-and-hold circuit 42 which may, for example, be the LF198 monolithic sample-and-hold circuit. The selected sample-and-hold circuit is coupled in such a way that when a suitable peak sample-and-hold strobe signal (PSH strobe) 43 is received, the peak sample-and-hold circuit 42 will continuously sample the receiver output signal 40 and will hold the peak value of that receiver output signal 40 occurring during the strobe time.

Of course, it is also possible to replace the peak sample-and-hold circuit with an integrator to measure the decay rate by integrating the normalized received ring signal for a fixed period of time and then comparing the result with a predefined standard value or otherwise converting the reading according to an imperically derived formula or look-up table to obtain a parameter reading. Alternatively, one cycle of the received ring signal could be integrated at two different times with the ratio being generated as a measure of decay rate and hence circuit Q. A predetermined imperically generated functional relationship or look up table could then be used to relate the generated ratio to the parameter in question.

Returning to FIG. 1, the held voltage signal from the peak sample-and-hold circuit 42 as shown in FIG. 1 is coupled to an analog-to-digital converter 44 which converts the analog voltage signal to a digital number. The digital number is inputted to the microprocessor 20 along a plurality of data lines 46 in response to an analog-to-digital strobe signal (A/D strobe) 45 occurring at a later time period. Suitable analog-to-digital converters are well known off-the-shelf devices and will therefore not be further described herein. The microprocessor 20 generates the PSH strobe signal 43 and the A/D strobe signal 45 upon the occurrence of preselected count values in the microprocessor counter.

The digitized number received by the microprocessor 20 is then compared against a preprogrammed normalization number. If the difference between the digitized number and the preprogrammed number is greater than a programmed tolerance value, the microprocessor 20 generates one of a pair of signals to alter the gain of the amplifier 36 to thereby alter the value of amplifier gain so that it more clearly corresponds to the preprogrammed number.

For example, in one embodiment, the microprocessor 20 generates a positive automatic gain pulse (+AGC) which has a pulse width proportional to the gain correction required to cause an increase in the gain of amplifier 36, and a negative automatic gain control pulse (−AGC) which has a pulse width proportional to the decrease in gain required to cause a decrease in the gain of the amplifier 26.

The positive automatic gain control signal +($\Delta$AGC) is coupled from the microprocessor 20 to the base of a field effect transistor 48 whose other terminals are coupled between a positive voltage source and ground through a capacitor 49. The negative automatic gain control signal (−$\Delta$AGC) is coupled to a base of a second field effect transistor 50 whose other terminals are coupled between a negative voltage source and ground through the capacitor 49. The output of the two field effect transistors 48 and 50 coupled to the capacitor 49 are also coupled to the positive input of an amplifier 52 whose output is coupled back to the negative input of the amplifier 52 in order to act as a voltage buffer to provide a high gain impedance from the capacitor in order to avoid leakage from the capacitor 49. The resultant signal from the output of the amplifier 52 is an analog automatic gain control signal which is coupled to vary the gain of the amplifier 36. The field effect transistors 48 and 50, the capacitor 49, and the amplifier 52 thus define a digital-to-analog converter which generates an analog gain control signal having a magnitude which depends on the pulse width of the digital automatic gain control signals +AGC and −AGC from the microprocessor 20.

It will be appreciated that in some embodiments of the invention where a ratio of a first value to a second value of the decaying received signal is computed as a measure of the decay rate, that accurate gain control for the amplifier is not required. Therefore, it may be possible to adjust the gain of amplifier manually without automatic gain control.

The indicator unit 10 may further include a suitable wave shaper 54 which is coupled to receive the receiver output signal 40 from the filter 38 to modify the receiver output signal into, for example, a square wave signal 55. The output of the wave shaper 54 is coupled to the phase-locked-loop 12 which may, for example, be the phase-locked-loop circuit having the part number CD4046A or any other suitable phase-locked-loop device well known in the art.

The phase-locked-loop device 12, includes a phase comparator 56 which has one input coupled to receive the square wave signal 55 from the wave shaper 54 and another input coupled to receive the VCO output signal 14. The phase of the VCO output signal 14 and the phase of the square wave signal 55 are compared in the phase comparator 56 and a phase correction signal 63 generated and fed back to the VCO 13 to control the phase of the VCO output signal 14. The phase correction signal 63 is an analog signal which has a voltage amplitude proportional to the amount of phase mismatch and is used to alter the phase and frequency of the output signal 14 match the phase and frequency of the received signal 40.

If the two signals inputted to the phase comparator 56 are matched in both phase and frequency, the phase comparator generates a digital phase compare signal 57. The above-described analog phase correction signal 63 and phase compare signal 57 are available outputs on many currently available off-the-shelf phase-locked-loop circuits.

Ordinarily, the phase-locked-loop operates continuously to adjust the phase and frequency of the voltage controlled oscillator signal 14 to match the phase of an input or received signal 40. However, in the present invention, it is possible, and even expected, that the received output signal 40 will become entirely damped and that there will be no input signal 40 against which the VCO signal 14 can be phase adjusted. To eliminate this potential problem, the analog phase correction signal 63 is only intermittently fed back to the VCO 13 during periods when it is known that the signal 55 will be oscillating.

To achieve this result, the phase correction signal 63 from the phase comparator 56 is coupled to a suitable analog switch 58 which is operable in response to an automatic frequency control (AFC) strobe signal 59 generated by the microprocessor 20 only during the time that the count on the microprocessor counter has certain predefined values. Phase adjustment occurs only during a positive going AFC strobe signal which closes the analog switch 58. A capacitor 60 is coupled between ground and switch 58 to maintain a constant voltage at the VCO input of the phase-locked-loop circuit 12 when the switch 58 is opened. A high impedance amplifier 61 may be coupled between the switch 58 and the VCO input.

The phase compare signal 57 from the phase comparator 56 is coupled to the microprocessor 20. The microprocessor 20 periodically samples the phase compare signal and when it has a value indicating the receiver output signal 40 and the VCO output signal 14 are in phase, will enable the display of a computed temperature value in a conventional digital display device 66 coupled to the microprocessor 20.

The microprocessor 20 may be any suitable off-the-shelf programable microprocessor and may for example be a National Semiconductor COP420C single cip CMOS Microcontroller.

Figure 6A:
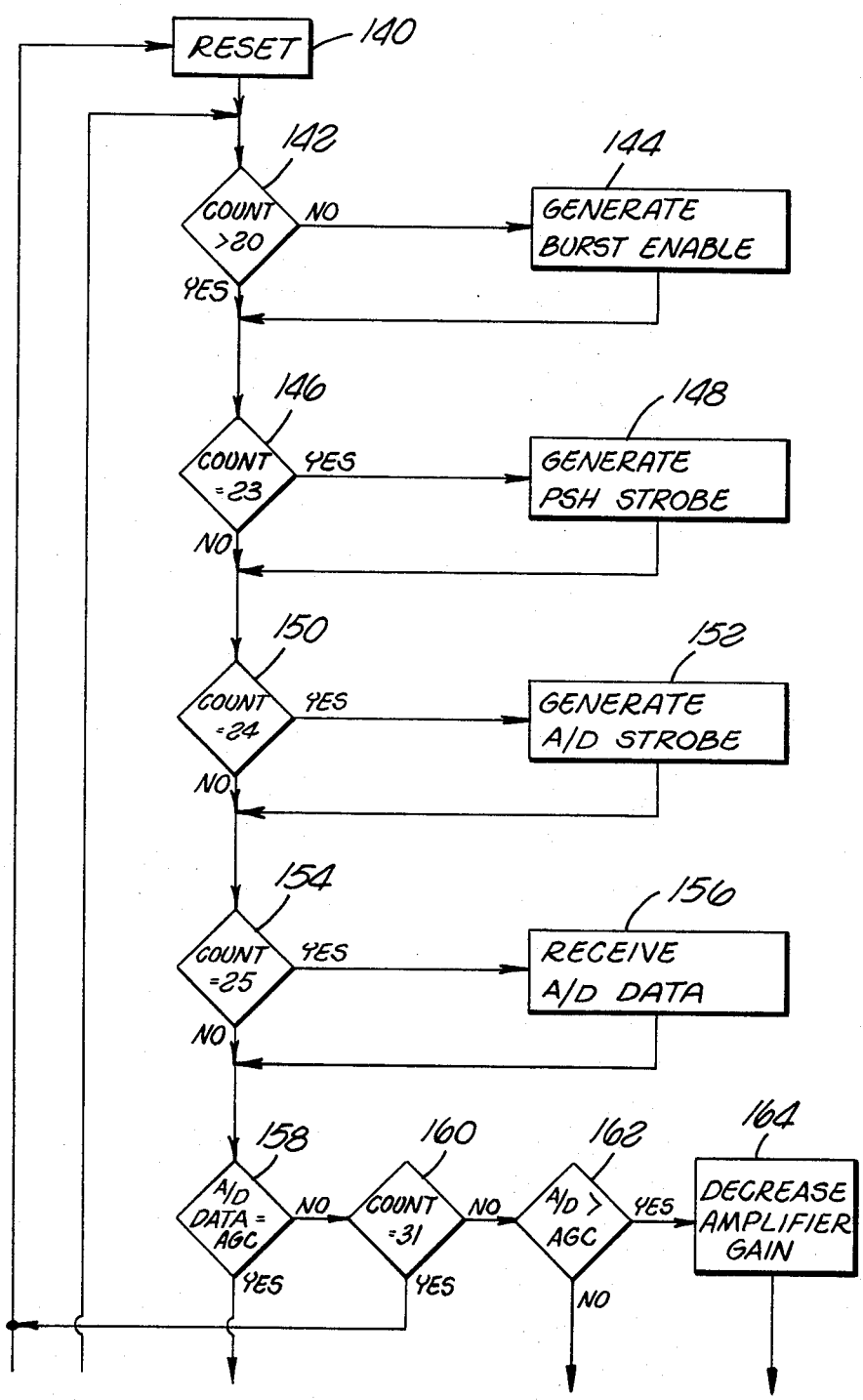
FIGS. 6A and 6B illustrate a simplified flow chart of a microprocessor program which may be used to generate various strobe signals and to perform various computations in accordance with the embodiment of the invention shown in FIG. 1.
Figure 6B:
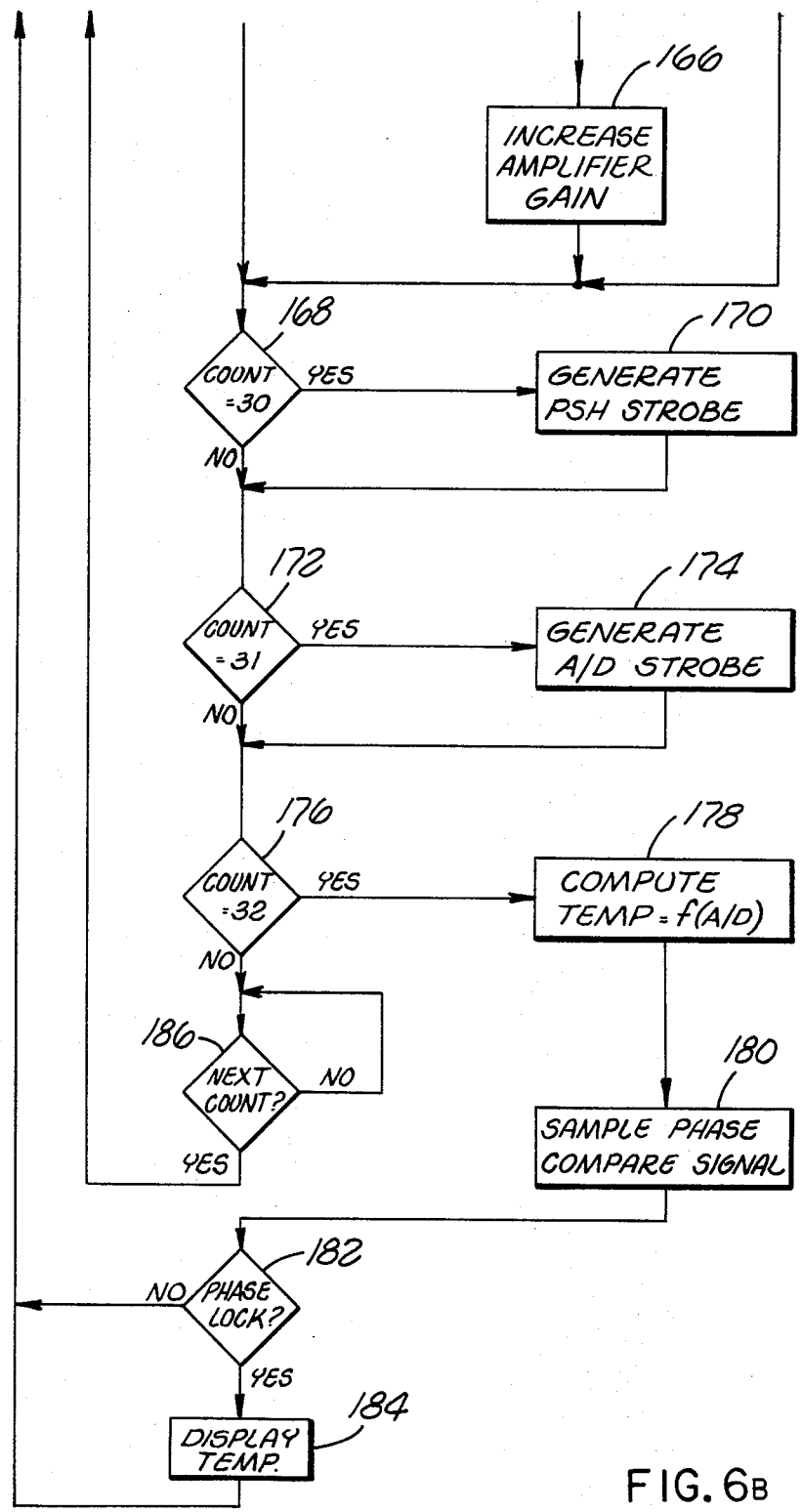

The microprocessor 20 may be programmed in accordance with the flow chart of FIGS. 6A and 6B to initially reset (block 140) the counter to zero. Thereafter, the microprocessor 20 is cycled through the program each time the counter increments. On each cycle through the program the count on the counter is first tested in block 142 and if the count is less than, for example, twenty, the microprocessor generates (block 144) the burst enable signal 24 used to open and close switch 22 (FIG. 1). Next, the count is tested in block 146 and if the count equals, for example, twenty-three, the PSH strobe signal 43 is generated (block 148) to enable sampling by the peak sample-and-hold circuit 42 (FIG. 1). The count is next tested in block 150 and if equal to twenty-four the microprocessor 20 generates (block 152) the A/D strobe pulse 45 to enable transfer of the digitized signal from the sample-and-hold circuit 42 to the A/D converter 44. Thereafter, the count is again tested in block 154 and if equal to twenty-five, the microprocessor 20 is internally enabled to receive (block 156) the data from the digital-to-analog converter 44 along data lines 46 and to store that data in a suitable memory in the microprocessor 20.

Prior to commencing the operation of the program, a preprogrammed automatic gain control number (preset AGC) is stored in a memory location in the microprocessor 20. The digitized signal (A/D data) representative of the peak value of the received output signal which occurs during the PSH strobe time, is next compared (block 158) against the preset AGC value. If the digitized A/D data is equal to the preset AGC value or is within a predefined tolerance of the preset AGC value, then no adjustment in the gain of the amplifier 36 is required and the program continues. However, if the A/D data is not equal to or within a predefined tolerance of the preset AGC value as shown in block 158, and the count on the counter is not equal to thirty-one (block 160), then the microprocessor determines (block 162) whether the value of the A/D data is greater or less than the preset AGC value. If the A/D data value is greater than the preset AGC value, then the amplifier gain is set too high and the microprocessor generates (block 164) a digital pulse signal −ΔAGC having a pulse width proportional to the amount of error in the amplifier gain to decrease the gain of amplifier 36 as above described. Conversely, if the A/D data value is less than the preset AGC value, then the microprocessor generates (block 166) a digital pulse signal +ΔAGC having a pulse width proportional to the amount by which the amplitude of the received signal 40 is below the preset AGC value to increase the amplifier gain. If the A/D data value is not substantially equal to the preset AGC value when the count reaches thirty-one (block 160), the microprocessor immediately resets the counter (block 140) and the program sequence is reinitiated.

The adjustment of the amplifier gain in the above manner continues until the sampled peak value at count twenty-three (block 146) on the microprocessor counter generates an A/D data value substantially equal to (or at least within an acceptable tolerance) of the preset AGC value. No temperature reading will be displayed until the peak value at count twenty-three substantially matches the preset AGC value.

If the sampled peak value at count twenty-three, i.e., the A/D data value, is substantially equal to the preset AGC value as above described, the microprocessor generates a second PSH strobe when the count of the counter is equal to thirty as indicated in blocks 168 and 170. The peak value of the received output signal 40 when the clock count is equal to thirty is then converted to a digital number upon the generation of a second A/D strobe when the count is thirty-one as shown in blocks 172 and 174. Thereafter, if the count is not equal to thirty-two (block 176), the microprocessor waits (block 186) until the counter is incremented by the next clock pulse and then repeats the program sequence starting at block 142. If the count is equal to 32, however, the microprocessor computes the temperature based upon a predefined and stored functional relationship (herein f(A/D)) between the temperature and the sampled peak value (A/D data) of the receiver output signal 40 as shown in block 176 and 178.

The functional relationship f(A/D) between temperature and the peak value of the receiver output signal 40 is predetermined and may be a nonlinear or linear relationship depending on the linearlity of the thermistor utilized in the sensor circuit. The particular functional relationship may be determined empirically by measuring the outputtted A/D value at several known temperatures and then storing that data to provide a mapping relationship between the peak value voltage and temperature.

It will be appreciated, of course, that since the processor adjusts the gain of the receiver amplifier at the first sample-and-hold period (count twenty-three) to be the same for all temperature values, the second peak value sample (count 30) will, by itself, be a measure of the ratio of the two received signal peak value samples and therefore a measure of the decay rate of the received signal 40.

After calculating the temperature according to the functional relationship F(A/D), the microprocessor 20 samples (block 180) the phase compare signal 57 from the phase-locked-loop 12. As indicated in block 182, if the phase compare signal indicates that the receiver output signal 40 and the VCO output signal 14 are in phase (i.e., phase locked) then the computed temperature is displayed (block 184) on a display device 66. After displaying the temperature, the counter of the microprocessor is reset in block 140 and the operation sequence repeated. If the receiver output signal 40 and the VCO output signal 14 are not in phase as indicated by the phase compare signal 57, the counter is immediately reset (block 140) without displaying the temperature and the program sequence repeated until the phase locked condition is achieved by the phase-locked-loop 12.

Therefore, a temperature value will be displayed only if the gain of the amplifier 36 is selected so that the peak value of the received signal sampled during count twenty-three is substantially equal to the preset AGC value stored in the microprocessor and the receiver output signal 40 is in phase with the voltage controlled oscillator output signal 14.

Of course, it will be appreciated that various other count numbers may be used to generate the above described or other signals. Additionally, it may be desired to obtain a plurality of temperature values as described in block 178 and then average those values to obtain the temperature value which will be displayed. Such a modification could be made by simply providing a second counter which increments once for each temperature value computed and then averages all values when the counter reaches a preprogrammed count value.

What is claimed is:

1. A telemetering system for measuring a selected physical parameter of an object comprising:
   an indicator device comprising:
      an oscillator for generating an oscillating first signal,
      means for intermittently transmitting a signal burst comprising a selected number of oscillations of the first signal,
      means for receiving a second oscillating signal,
      means for selecting one of the oscillations of the second signal occurring after the end of each signal burst,
      means for measuring peak values for measuring the peak value of the selected one oscillation, and
      means for displaying the measured peak value for indicating the value of the selected physical parameter; and
   a passive but energy storing sensor circuit having associated therewith a variable figure-of-merit-of energy-storage (Q) for being excited by the transmitted excitation energy of the first signal to store a portion of the excitation energy and transmit a second signal having a parameter value dependent on the amount of excitation energy stored in the sensor circuit, the stored energy dissipating from the sensor circuit as a consequence of the transmission of the transmitted second signal, the rate of stored energy dissipation being dependent on the value of Q, the sensor circuit comprising:
      a first parallel tuned circuit having a resonant frequency for being rung by each signal burst from the indicator device, the tuned circuit transmitting the ringing to define the second signal, and
      a selected parameter sensitive member coupled in the tuned circuit for altering the shape of the ring down and therefore the peak value of each oscillation of the second signal after the end of each signal burst, the parameter sensitive member being attached in parameter sensing relationship to the object.

2. The telemetering system of claim 1 wherein the first tuned circuit comprises:
   a capacitor, and
   an inductor coupled in parallel with the capacitor, the parameter sensitive member being coupled in parallel with both the capacitor and the inductor.

3. The telemetering system of claims 1 or 2 wherein the parameter sensitive member is a thermistor.

4. The telemetering system of claim 3 wherein the indicator device further comprises phase-locked-loop means coupled for adjusting the phase and frequency of the first signal to match the phase and frequency of the second signal received from the sensor circuit and generating a phase locked signal when the first and second signals are in phase.

5. The telemetering system of claim 1 or 2 wherein the indicator device further comprises:
  variable gain amplifier means coupled to the receiver for amplifying the received second signal;
  means for altering the gain of the amplifier to vary the amplitude of the second signal outputted from the amplifier means;
  means for selecting another of the oscillations of the second signal outputted from the amplifier means and measuring the peak value of the selected other oscillation in the measuring means;
  means for comparing the peak value of the selected other oscillation against a predefined calibration value and generating a gain control signal representative of the difference between the peak value and the calibration value, the gain control signal coupled to alter the gain of the amplifier means and generate a compare signal when the peak value of the selected other oscillation matches the predefined calibration value.

6. The telemetering system of claim 5 wherein the indicator device further comprises:
  second means for enabling display of the measured peak value of the selected one oscillation only when the means for comparing generates the compare signal.

7. The telemetering system of claims 1 or 2 wherein the selected parameter sensitive member alters the duration of the ringing in nonlinear relationship to variations in the value of the selected physical parameter, the indicator device further comprising means for modifying the measured peak value of the selected one oscillation in accordance with the nonlinear relationship prior to displaying the measured peak value on the means for displaying.

8. The telemetering system of claim 1 wherein the indicator device further comprises phase-locked-loop means coupled for adjusting the phase and frequency of the first signal to match the phase and frequency of the second signal received from the sensor circuit and generating a phase locked signal when the first and second signals are in phase.

9. The telemetering system of claim 8 wherein the indicator device further comprises:
  variable gain amplifier means coupled to the receiver for amplifying the received second signal;
  means for altering the gain of the amplifier to vary the amplitude of the second signal outputted from the amplifier means;
  means for selecting another of the oscillations of the second signal outputted from the amplifier means and measuring the peak value of the selected other oscillation in the measuring means;
  means for comparing the peak value of the selected other oscillation against a predefined calibration value and generating a gain control signal representative of the difference between the peak value and the calibration value, the gain control signal coupled to alter the gain of the amplifier means and generate a compare signal when the peak value of the selected other oscillation matches the predefined calibration value.

10. The telemetering system of claim 9 wherein the indicator device further comprises first means for enabling display of the measured peak value of the selected one oscillation only when the phase lock signal is generated.

11. The telemetering system of claim 10 wherein the indicator device further comprises:
  second means for enabling display of the measured peak value of the selected one oscillation only when the means for comparing generates the compare signal.

12. The telemetering system of claim 8 wherein the indicator device further comprises first means for enabling display of the measured peak value of the selected one oscillation only when the phase lock signal is generated.

13. A telemetering system for measuring a selected physical parameter of an object comprising:
  a transmitter for intermittently transmitting a burst of oscillating circuit excitation energy wherein the burst of circuit excitation energy has a predefined number of oscillations;
  a passive but energy storing sensor circuit for being excited by the burst of circuit excitation energy from the transmitter to store a portion of the circuit excitation energy and thereafter transmit a first oscillating signal, the stored energy dissipating from the sensor circuit after the end of each burst of circuit excitation energy in response to the transmission of the first signal, the rate at which the dissipation occurs defining a decay rate which is dependent on the figure-of-merit of energy storage of the sensor circuit, the sensor circuit comprising:
    a sensor component coupled in the sensor circuit and positioned in parameter sensing relationship to the object, the sensor component having an impedance which varies in response to variations in the physical parameter to cause variations to occur in the figure-of-merit of energy storage to thereby alter the rate at which the stored energy in the sensor circuit is dissipated by the transmission of the first signal by the sensor circuit, whereby the rate of dissipation is indicative of the value of the physical parameter;
  a receiver for receiving the first signal transmitted from the sensor circuit comprising:
    means for measuring the decay rate of the received first signal after termination of each burst of circuit excitation energy, the measured decay rate being indicative of the rate at which the stored energy in the sensor circuit is dissipated during the time after the termination of the burst of energy;
    means for displaying the measured decay rate for indicating the value of the selected parameter.

14. A telemetering system for measuring a selected physical parameter of a biological object comprising:
  an indicator device comprising:
    a voltage controlled oscillator for generating a first signal oscillating at a first frequency,
    a transmitter for transmitting a second signal comprising a plurality of intermittent bursts of the first signal, each burst having a predefined number of oscillations of the first signal,
    a receiver for receiving and amplifying a third signal oscillating at a second frequency, a peak value sample-and-hold circuit coupled to sample and hold the peak value of selected oscillations of the third signal, a processor coupled to the oscillator for repetitively counting a selected number of oscillations of the first signal starting at count N0 and continuing up to a maximum count of NM and generating a transmit enable signal when the count is equal to N3 where $N1 \leqq N3 \leqq N2$ and $N0 \leqq N1 < N2 < NM$, each burst of the second signal being generated when the transmit enable signal is generated; generating a first sample enable signal when the count number is N4 where $N2 < N4 \leqq NM$, the peak sample and hold circuit being coupled to the first sample enable signal to sample and hold the peak amplitude of the oscillation of the third signal occurring when the count number is N4, and a display device coupled for displaying the value of the peak amplitude of the oscillation of the third signal occurring when the count number is N4; and a passive but energy storing sensor circuit having associated therewith a variable figure-of-merit-of-energy storage (Q) for being excited by the transmitted excitation energy of the second signal to store a portion of the excitation energy and transmit a third signal having a parameter value dependent on the amount of excitation energy stored in the sensor circuit, the stored energy dissipating from the sensor circuit as a consequence of the transmission of the third signal, the rate of stored energy dissipation being dependent on the value of Q, the sensor circuit comprising:

a first tuned circuit having a resonant frequency for being rung by each burst of the second signal, the ringing of the first tuned circuit continuing after the end of each burst of the second signal whereby the third signal is transmitted from the sensor circuit, and a selected parameter sensitive member coupled in the tuned circuit for altering the shape of the ring down after the end of each second signal burst, the parameter sensitive member being attached in parameter sensing relationship to the biological object.

15. The telemetering system of claim 14 wherein the processor further comprises means for generating an amplifier gain control (AGC) signal comprising:
a memory for storing a preset AGC value;
means for generating a second sample enable signal when the count number is N5 where $N4 < N5 < NM$, the peak value sample-and-hold circuit coupled for being activated by the second sample enable signal to sample and hold the peak amplitude of the oscillation of the third signal occurring when the count number is N5;
means for comparing the stored preset AGC value and the peak value of the third signal oscillation sampled and held when the count number is N5 and generating a gain control signal if the preset AGC value and the sampled peak value do not compare, the gain control signal coupled to the receiver to alter the amplification of the third signal received by the receiver until the peak value sampled and held at count N5 matches the preset AGC value.

16. The telemetering system of claims 14 or 15 wherein the indicator device further comprises:
phase-locked-loop means coupled for adjusting the phase and frequency of the first signal and generating a phase lock signal when the phase and frequency of the first signal matches the phase and frequency of the third signal, the phase lock signal coupled to the processor for enabling the display device to display the peak value of the oscillation of the third signal occurring when the count number is N5.

17. A telemetering system for measuring a selected physical parameter comprising:
a passive but energy storing sensor circuit having at least one parameter sensitive component coupled for altering the Q of the sensor circuit, the sensor circuit having a selected resonant frequency;
means for intermittently transmitting a burst of oscillating energy for causing the sensor circuit to ring at its resonant frequency for defining a ring signal;
means for remotely sensing the ring signal after the end of each transmitted burst and generating a received signal therefrom;
means for measuring the decay rate of the ring signal after the end of each transmitted burst, said decay rate being a function of the Q of the sensor circuit;
means for normalizing whereby the amplitude of the received signal is altered to be substantially equal to a predefined value at a first selected time after the end of each transmitted burst;
means for altering the phase of the transmitted burst to be in phase with the received signal; and
means for displaying the masure of the decay rate of the received signal.

18. The telemetering system of claim 17 wherein the means for displaying is interconnected to the means for normalizing and the means for altering whereby the means for displaying is operable to display the measure of the peak amplitude only when the transmitted burst is in phase with the received signal and the peak amplitude of the received signal at the first preselected time is substantially equal to the predefined value.

19. The telemetering system of claim 17 wherein the means for normalizing comprises means for adjusting the amplitude of the transmitted burst.

20. A telemetering system for measuring a selected physical parameter of an object comprising:
a passive but energy storing sensor circuit having associated therewith a variable figure-of-merit-of-energy storage (Q) for being excited by the transmitted excitation energy to store a portion of the excitation energy and retransmit a signal having a parameter value dependent on the amount of excitation energy stored in the sensor circuit, the stored energy dissipating from the sensor circuit as a consequence of the transmission of the retransmitted signal, the rate of stored energy dissipation being dependent on the value of Q, the sensor circuit comprising:
a tuned circuit for being rung at its resonant frequency by an oscillating electromagnetic energy signal to define a ring signal, and retransmitting the ring signal, and
sensor means coupled in the tuned circuit for altering the figure-of-merit of energy storage of the tuned circuit in response to variations in the physical parameter, the ring signal decaying at a rate proportional the figure-of-merit of energy storage after termination of the oscillating electromagnetic energy signal by which the tuned circuit was rung;

an indicator device comprising:

transmitter means for transmitting intermittent bursts of the oscillating electromagnetic energy to intermittently ring the tuned circuit at its resonant frequency, receiver means for receiving the retransmitted ring signal, means for measuring the rate-of-decay of the ring signal after termination of each intermittent burst of the oscillating electromagnetic energy for measuring the figure of merit of energy storage of the tuned circuit, means for computing a measure of the physical parameter from the measure of the rate-of-decay of the ring signal according to a predefined functional relationship, and means for displaying the measure of the physical parameter.

21. The telemetering system of claim 20 wherein the means for measuring comprises:

means for measuring the peak value of the ring signal occurring during a first predefined time interval after termination of the transmission of each burst of the oscillating electromagnetic energy;

means for measuring the peak value of the ring signal occurring during a second predefined time interval after the first time interval but before the commencement of the next burst of oscillating electromagnetic energy, and means for generating a ratio of the first peak value and the second peak value, the ratio being said measure of the rate-of-decay of the ring signal.

22. A telemetering system for measuring a selected physical parameter of an object comprising:

a transmitter for transmitting excitation energy;

a sensor circuit having associated therewith a variable figure-of-merit-of-energy-storage (Q) for being excited by the excitation energy from the transmitter to store a portion of the excitation energy and transmit a first signal having a parameter value dependent on the amount of excitation energy stored in the sensor circuit, the stored energy dissipating from the sensor circuit as a consequence of the transmission of the first signal, the rate of stored energy dissipation being dependent on the value of Q, the sensor circuit comprising:

a parallel tuned circuit, and a sensor component shunting the parallel tuned circuit and positioned in parameter sensing relationship to the object, the sensor component having an impedance which varies in response to variations in the physical parameter to cause variations in the Q according to a fixed relationship whereby the measure of the signal parameter is indicative of the value of the physical parameter; and a receiver for receiving the first signal and measuring signal parameter of the first signal to obtain a measure of the Q indicative of the value of the physical parameter.

23. A telemetering system for remotely measuring a selected physical parameter of an object comprising:

a passive but energy storing sensor circuit having associated therewith a variable figure-of-merit-of-energy-storage (Q) for being excited by transmitted excitation energy to store a portion of the excitation energy and retransmit a signal having a parameter value dependent on the amount of excitation energy stored in the sensor circuit, the stored energy dissipating from the sensor circuit as a consequence of the transmission of the retransmitted signal, the rate of stored energy dissipation being dependent on the value of Q, the sensor circuit comprising:

a parallel tuned circuit, and a sensor component positioned in physical parameter sensing relationship to the object and coupled in the parallel tuned circuit to alter the Q of the sensor in response to variations in the physical parameter whereby the value of the Q of the sensor circuit is indicative of the value of the physical parameter; and means for remotely measuring the Q of the sensor circuit to obtain the value of the physical paramenter therefrom.

24. A telemetering system for remotely measuring a selected physical parameter of an object comprising:

a passive but energy storing sensor circuit having associated therewith a variable figure-of-merit-of-energy-storage (Q) for being excited by transmitted excitation energy to store a portion of the excitation energy and retransmit a signal having a parameter value dependent on the amount of excitation energy stored in the sensor circuit, the stored energy dissipating from the sensor circuit as a consequence of the transmission of the retransmitted signal, the rate of stored energy dissipation being dependent on the value of Q, the sensor circuit comprising:

a parallel tuned circuit, and a sensor component positioned in physical parameter sensing relationship to the object and coupled in the parallel tuned circuit to alter the Q of the parallel tuned circuit in response to variations in the physical parameter, whereby the value of the Q of the parallel tuned circuit is indicative of the value of the physical parameter.

25. The sensor of claim 24 wherein the parallel tuned circuit comprises a capacitor and an inductor coupled in parallel with each other.

26. The sensor of claims 24 or 25 wherein the physical parameter to be measured is the temperature of the object and the sensor component comprises a thermistor.

27. The sensor of claims 24 or 25 wherein the sensor component comprises a capacitor with a parameter sensitive dielectric.

28. The sensor of claim 24 or 25 wherein the sensor component comprises an inductor coil with a parameter sensitive core.

29. A sensor useful in measuring a physical parameter of an object comprising:

a passive but energy storing sensor circuit having associated therewith a variable figure-of-merit-of-energy-storage (Q) for being excited by transmitted excitation energy to store a portion of the excitation energy and retransmit a signal having a parameter value dependent on the amount of excitation energy stored in the sensor circuit, the stored energy dissipating from the sensor circuit as a consequence of the transmission of the retransmitted signal, the rate of stored energy dissipation being dependent on the value of Q, the sensor circuit comprising a parameter sensitive element for being positioned in physical parameter sensing relationship to the object and coupled in the passive circuit to alter the Q of the passive circuit in response to variations in the physical parameter, whereby the value of Q of the passive circuit is indicative of the value of the physical parameter.

30. The sensor circuit of claim 29 wherein the parameter sensitive element comprises a thermistor.

31. The sensor circuit of claim 30 wherein the thermistor is coupled in parallel with the passive circuit.

32. The sensor circuit of claim 29 wherein the passive circuit includes a capacitive component and the parameter sensitive element comprises a parameter sensitive dielectric in the capacitive component.

33. The sensor circuit of claim 29 wherein the passive circuit includes an inductive coil component and the parameter sensitive element comprises a parameter sensitive core in the inductive coil component.

34. A telemetering system for measuring the value of a selected physical parameter of an object comprising:
a sensor comprising:
a passive but energy storing sensor circuit having associated therewith a variable figure-of-merit-of-energy-storage (Q) for being excited by transmitted excitation energy to store a portion of the excitation energy and retransmit a signal having a parameter value dependent on the amount of excitation energy stored in the sensor circuit as a consequence of the transmission of the retransmitted signal, the rate of stored energy dissipation being dependent on the value of Q, the sensor circuit comprising a parameter sensitive element for being positioned in physical parameter sensing relationship to the object and coupled in the passive circuit to alter the Q of the passive circuit in response to variations in the physical parameter, whereby the value of Q of the passive circuit is indicative of the value of the physical parameter;
means for energizing the sensor to store energy in the passive circuit, the sensor dissipating the energy stored therein in proportion to the value of Q of the sensor; and
means for measuring the energy dissipation of the sensor to obtain a measure of the value of Q and therefrom a measure of the value of the physical parameter.

35. The telemetering system of claim 34 wherein the parameter sensitive element comprises a thermistor.

36. The telemetering system of claim 35 wherein the thermistor is coupled in parallel with the passive circuit.

37. The telemetering system of claim 34 wherein the passive circuit includes a capacitive component and the parameter sensitive element comprises a parameter sensitive dielectric in the capacitive component.

38. The sensor circuit of claim 34 wherein the passive circuit includes an inductive coil component and the parameter sensitive element comprises a parameter sensitive core in the inductive coil component.

39. The telemetering system of claim 34 wherein the means for energizing comprises a transmitter for intermittently transmitting a burst of energy to excite the sensor whereby the sensor intermittently dissipates energy in the form of a transmitted first signal and the means for measuring comprises a receiver for sensing the periodically transmitted first signal from the sensor and obtaining therefrom a measure of the Q of the sensor circuit.

40. A method of measuring the value of a physical parameter of an object using a sensor having a passive but energy storing circuit characterized by a figure of merit of energy storage (Q), and a parameter sensitive element coupled in the passive circuit to alter the Q of the passive circuit in response to variations in the physical parameter comprising the steps of:
(1) affixing the sensor to the object;
(2) energizing the sensor for storing the energizing energy;
(3) reradiating the energy stored in the passive circuit to cause the stored energy to be dissipated, the rate of dissipation being indicative of the value of Q of the sensor circuit;
(4) receiving the radiated energy from the sensor; and
(5) measuring the radiated energy received to obtain a measure of Q of the sensor.

41. A method of measuring the value of a physical parameter of an object comprising:
affixing to an object a sensor having a passive but energy storing circuit characterized by a figure-of-merit-of-energy-storage (Q) which is variable in response to variations in the physical parameter to the object;
energizing the sensor to radiate a signal comprising a measure of the Q of the sensor;
receiving the signal from the sensor; and
obtaining the value of Q from the signal to obtain a measure of the value of the physical parameter.

42. A telemetering system for measuring a selected physical parameter of an object comprising:
a sensor circuit comprising:
a tuned circuit for being rung at its resonant frequency by an oscillating electromagnetic energy signal to define a ring signal, and retransmitting the ring signal; and
sensor means coupled in the tuned circuit for altering the figure-of-merit of energy storage of the tuned circuit in response to variations in the physical parameter, the ring signal decaying at a rate proportional the figure-of-merit of energy storage after termination of the oscillating electromagnetic energy signal by which the tuned circuit was rung; an indicator device comprising:
transmitter means for transmitting intermittent bursts of the oscillating electromagnetic energy to intermittently ring the tuned circuit at its resonant frequency;
receiver means for receiving the retransmitted ring signal;
means for measuring the rate-of-decay of the ring signal after termination of each intermittent burst of the oscillating electro-magnetic energy for measuring the figure of merit of energy storage of the tuned circuit, said means for measuring comprising means for measuring the value of the ring signal occurring during a first predefined time interval after termination of the transmission of each burst of the oscillating electromagnetic energy, means for measuring the value of the ring signal occurring during a second predefined time interval after the first time interval but before the commencement of the next burst of oscillating electromagnetic energy, and means for generating a ratio of the first value and the second value, the ratio being said measure of the rate-of-decay of the ring signal;
means for computing a measure of the physical parameter from the measure of the rate-of-decay of the ring signal according to a predetermined functional relationship; and
means for displaying the measure of the physical parameter.

* * * * *

UNITED STATES PATENT AND TRADEMARK OFFICE
CERTIFICATE OF CORRECTION

PATENT NO. : 4,531,526
DATED : July 30, 1985
INVENTOR(S) : Leonard J. Genest

It is certified that error appears in the above-identified patent and that said Letters Patent are hereby corrected as shown below:

| Col. | Line | |
|---|---|---|
| 1 | 24 | "constitues" should be --constitutes--; |
| 1 | 33 | "Murate" should be --Murata--; |
| 1 | 67 | first "the" should be --of--; |
| 3 | 36 | ",a)" should be --), a--; |
| 4 | 37 | after "Figs." should be --2-4, 7 and 8--; |
| 4 | 40 | "and" should be deleted; |
| 6 | 26 | after "capability" should be --of the indicator unit to alter the frequency of the--; |
| 11 | 40 | "outputtted" should be --outputted--; |
| 20 | 64 | "predetermined" should be --predefined--. |

Signed and Sealed this

Third Day of December 1985

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,531,526
DATED : July 30, 1985
INVENTOR(S) : Leonard J. Genest

It is certified that error appears in the above–identified patent and that said Letters Patent are hereby corrected as shown below:

| Col. | Line | |
|---|---|---|
| 1 | 22 | "in" should be --is--; |
| 16 | 33 | "masure" should be --measure--. |

Signed and Sealed this

Twenty-eighth Day of October, 1986

[SEAL]

*Attest:*

DONALD J. QUIGG

*Attesting Officer*     *Commissioner of Patents and Trademarks*